(12) United States Patent
Srivastava et al.

(10) Patent No.: US 6,893,668 B2
(45) Date of Patent: May 17, 2005

(54) PROCESS FOR ISOLATION OF ANTICANCER AGENT CAMPTOTHECIN FROM *NOTHAPODYTES FOETIDA*

(75) Inventors: Santosh Kumar Srivastava, Uttar Pradesh (IN); Merajuddin Khan, Uttar Pradesh (IN); Suman Preet Singh Khanuja, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 130 days.

(21) Appl. No.: 10/402,149

(22) Filed: Mar. 31, 2003

(65) Prior Publication Data

US 2004/0192917 A1 Sep. 30, 2004

(51) Int. Cl.$^7$ .......................... A61K 35/78; A61K 31/44
(52) U.S. Cl. ...................... 424/779; 424/725; 514/279; 514/280; 514/285; 546/23; 546/48
(58) Field of Search .................... 424/725, 779; 514/279, 280, 285; 546/23, 48

(56) References Cited

U.S. PATENT DOCUMENTS

| | | | | |
|---|---|---|---|---|
| 5,352,789 A | * | 10/1994 | Hinz | 546/48 |
| 5,525,609 A | * | 6/1996 | Bombardelli et al. | 514/285 |
| 5,527,913 A | * | 6/1996 | Hinz | 546/48 |
| 5,608,066 A | * | 3/1997 | Hinz | 546/48 |
| 5,786,344 A | * | 7/1998 | Ratain et al. | 514/100 |
| 6,046,209 A | * | 4/2000 | Berges et al. | 514/279 |
| 6,107,486 A | * | 8/2000 | Hinz | 546/48 |
| 6,156,897 A | * | 12/2000 | Hinz | 546/48 |
| 6,218,540 B1 | * | 4/2001 | Ciufolini et al. | 546/23 |

FOREIGN PATENT DOCUMENTS

| | | | |
|---|---|---|---|
| JP | 61200902 | * | 9/1986 |
| JP | 01061482 | * | 3/1989 |

OTHER PUBLICATIONS

Govindachari et al. Phytochemistry. 1972. vol. 11, No. 12, pp. 3529–3531.*

* cited by examiner

*Primary Examiner*—Christopher R. Tate
(74) *Attorney, Agent, or Firm*—Nixon & Vanderhye P.C.

(57) ABSTRACT

The present invention relates to an improved and economical process for the isolation of anticancer agent Camptothecin from the twigs and stem of *Nothapodytes foetida* using hot extraction 20(S) Camptothecin is an alkaloid, which contains a pentacyclic ring system that includes a pyrrolo [3,4-b] quinoline moiety (ring A, B and C), the pyridone ring D and a chiral center at C-20 in ring E.

5 Claims, No Drawings

PROCESS FOR ISOLATION OF ANTICANCER AGENT CAMPTOTHECIN FROM *NOTHAPODYTES FOETIDA*

FIELD OF THE INVENTION

The present invention relates to an improved and economical process for isolation of anticancer agent Camptothecin from twigs and stem of *Nothapodytes foetida*. 20(S) Camptothecin is an alkaloid containing a pentacyclic ring system that includes a pyrrolo [3,4-b]quinoline moiety (ring A, B and C), a pyridone ring D and a chiral centre at C-20 in ring E.

BACKGROUND OF THE INVENTION

Camptothecin is one of the most impressive anticancer molecule of the recent years because it is the first compound found to directly block the topoisomerase (Topo-I), a DNA replication enzyme, thus stopping cell division. It was originally isolated from a rare Chinese plant *Camptotheca acuminata* Decne (Nyssacea) by Prof. Wall and co-workers in 1966 under the natural anticancer agent screening programme, carried out by the National Cancer Institute (NCI), USA.

Because of the noteworthy activities of camptothecin towards L 1210 in mice and walker 256 tumor in rats, camptothecin has been a molecule of great interest from the time of its initial isolation, but due to low solubility and high toxicity, its therapeutic utility was restricted for a long time in various parts of the world. However, at the same time it was used in China for the treatment of liver carcinoma and tumors of head and neck. Recently scientist around the world carried out tremendous work on the chemical transformation of camptothecin into analogs having potential anticancer activities, better solubility and less toxicity. Finally, success has been achieved and two camptothecin derived drugs, Topotecan (Hycamtin) and Irinotecan (CPT-II, Camptosar) have been approved by the FDA for the treatment of ovarian, lung and colorectal cancers. 9-Nitrocamptothecin (Orathecin) another camptothecin derived drug is expected to receive FDA approval for pancreactic cancer treatment soon. Simultaneously 9-Aminocamptothecin (9-AC) has also been introduced in clinical trials because it exhibited curative ability against human colon carcinoma and strong antitumor activity against solid tumor xenographts. There are 12 other camptothecin derived drugs, which showed promising results and are in clinical trials. Camptothecin anologs have also been demonstrated to be potent antiviral, anti-HIV agents and chemosterilants. Thus, camptothecin will have broader uses and worldwide demand of camptothecin (CPT) will dramatically increase.

Presently, CPT production relies primarily on the extracts from *Camptotheca acuminata* Decaisne. Although trees of *C. acuminata* grow fast but since many parts of this tree are being used for the extraction of camptothecin, *C. acuminata* is becoming endangered in many parts of the world, particularly in China.

In India camptothecin is being isolated from various parts of Indian *Nothapodytes foetida* (formerly *Mappia foetida*) Miers (Icacinaceae) in about 0.01–0.15%. *Nothapodytes foetida* is a small tree abundant in Western Ghats of India. Literature indicates many reports on distribution, isolation, characterization and biological activities of camptothecin and its various derivatives. Presently, camptothecin is mainly isolated from the roots of *Nothapodytes foetida*, To isolate 1 Kg of camptothecin, more than 1000 Kg of roots are required, thus leading to uprooting or destruction of several thousands of plants.

This destruction method of camptothecin isolation from the roots of *N. foetida* is the biggest drawback of the existing processes. This prompted us to research into a non-destructive method of camptothecin isolation and develop an easy and economical process for isolation of this anticancer agent, thereby bringing it within the reach of the common people.

A literature survey revealed that an isolation procedure for camptothecin from stem of *Mappia foetida* syn *Nothapodytes foetida* ("Alkaloids of *Mappia foetida*", Govindachari and Visvanathan, 1972, *Phytochenmistry*, 11, 3529–3531) has been reported. The process involved defatting of powdered stem twice with hexane followed by successive cold extraction thrice with $Me_2CO$ and MeOH Extracts were combined separately, concentrated under vacuum and left in ice chest for a week to give a greenish white solid, which on triangular crystallization results in the isolation of camptothecin in 0.11% yield.

The method described above suffers from a number of disadvantages. The biggest disadvantage of the above process is the poor yield of camptothecin (0.11%) when compared with ours (0.15%). The second disadvantage of the above method is that it uses cold percolation process where plant material is left over night in a solvent for each percolation, hence for complete extraction (twice with hexane, thrice with $Me_2CO$ and twice with MeOH) of plant material at least seven days are required. The third disadvantage of the above method is that it requires more solvent, more electricity, more manpower and more time, thus resulting in an expensive and time taking process for the isolation of camptothecin from the twigs and stem of *N. foetida*.

OBJECTS OF THE INVENTION

The main object of the invention is to provide an improved process for the isolation of camptothecin from the twigs and stem of *N. foetida*.

Another object of the invention is to avoid use of tedious and time taking extraction and purification processes for isolating camptothecin from the twigs and stem of *N. foetida*.

A further object of the invention is to provide an economical process for the isolation of camptothecin from the twigs and stem of *N. foetida*.

SUMMARY OF THE INVENTION

Accordingly the present invention provides an improved, and economical process for the isolation of camptothecin from the twigs and stem of *N. foetida*, which comprises of drying, grinding and hot defatting of *N. foetida* twigs and stems with light petroleum fraction followed by successive sequential hot extraction with two solvents selected from $CH_2Cl_2$, $CHCl_3$, EtOAc, ether, acetone, MeOH, EtOH and $CH_3CN$; removal of solvents under vacuum at a temperature in the range of 35–40° C., precipitation and filtration of crude extracts give camptothecin with up to 0.15% yield.

In one embodiment of the present invention a varied range of defatting solvents, petroleum ether, hexane, benzene, toluene and dichloromethane can be used.

In another embodiment of the present invention a varied range of solvents, chloroform, ethylacetate, ether, acetone, methanol, ethanol, acetonitrile and n-butanol can be used for the extraction of plant material.

DETAILED DESCRIPTION OF THE INVENTION

The present invention provides an improved and economical process for the isolation of camptothecin from the twigs and stem of N. foetida. The process comprises drying, grinding and hot defatting of N. foetida twigs and stems with a light petroleum fraction. This is followed by successive sequential hot extraction with two solvents selected from $CH_2Cl_2$, $CHCl_3$, EtOAc, ether, acetone, MeOH, EtOH and $CH_3CN$. The solvents are then removed under vacuum preferably at a temperature in the range of 35–40° C. The crude extract obtained thereby is then precipitated and filtered to obtain camptothecin with up to 0.15% yield.

The defatting of the twigs and stems of N. foetida can be carried out using a wide range of defatting solvents such as petroleum ether, hexane, benzene, toluene and dichloromethane. The extraction of the plant material to obtain the crude extract is preferably carried out with a solvent such as chloroform, ethylacetate, ether, acetone, methanol, ethanol, acetonitrile or n-butanol. The extraction is preferably carried out as hot extraction in a sequence of two steps using two solvents.

The following examples are given by way of illustration of the present invention and should not be construed to limit the scope of present invention.

EXAMPLE 1

The powdered twigs and stem (1 Kg) of N. foetida were first cold defatted with petroleum ether (bp 40–60° C.) in a percolator. Further extraction of defatted material was carried out with EtOAc and later by acetone. Removal of the solvent was carried out under vacuum at 35–40° C. Both EtOAc and $Me_2CO$ extracts on precipitation and filtration thrice resulted in the isolation of camptothecin in 0.085% yield.

EXAMPLE 2

The powdered twigs and stem (800 g) were first hot defatted with hexane in a Soxhlet extractor. Further extraction of the defatted material was successively carried out with $CHCl_3$ and $CH_3CN$. Removal of the solvent was carried out under vacuum at 35–40° C. Both $CHCl_3$ and $CH_3CN$ extracts on precipitation and filtration twice resulted in the isolation of camptothecin in 0.095% yield.

EXAMPLE 3

The powdered twigs and stem (2 Kg) were first cold defatted with petroleum ether (bp 40–60° C.) in a percolator. Further extraction of the defatted material was carried out first with acetone and later on with EtOH. Removal of the solvents was carried out under vacuum at 35–40° C. Both acetone and EtOH extracts on repeated precipitation and filtration thrice resulted in the isolation of camptothecin in 0.09% yield.

EXAMPLE 4

The powdered twigs and stem (1.5 Kg) were first hot defatted with hexane in Soxhlet extractor. Further extraction of the defatted material was successively carried out with EtOAc and MeOH. Both EtOAc and MeOH extracts on precipitation and filtration thrice resulted in the isolation of camptothecin in 0.10% yield.

Advantages

1. The present process uses simple precipitation and filtration methods for the purification of camptothecin, which are easy, less time taking and inexpensive, while in prior art process, extracts are kept in ice-chest for a week and uses tedious triangular crystallization for the isolation of camptothecin.
2. The use of hot Soxhlet extraction results in defatting and complete extraction of plant material being achieved in only one day, while defatting and extraction of plant material in prior art process requires more than seven days.
3. The process of the invention results in 36% yield advantage of camptothecin compared to that of prior art process.
4. The other advantages of our process are that it uses 2–7 times less amount of solvents, electricity, man power and time to that of prior art process.

We claim:

1. A process for the isolation of camptothecin from the twigs and stem of N. foetida, which comprises of drying, grinding N. foetida twigs and stems, subjecting the dried and ground N. foetida twigs and stems to hot defatting with a light petroleum fraction followed by hot extraction with a first solvent followed by hot extraction with a second solvent, removing the solvents under vacuum to obtain crude extracts of the plant material, precipitating and filtering the crude plant extracts to obtain camptothecin with up to 0.15% yield.

2. A process as claim 1 wherein the hot defatting is carried out using a solvent selected from the group consisting of petroleum ether, hexane, benzene, toluene and dichloromethane.

3. A process as claim 1 wherein the solvents used for successive sequential hot extraction are selected from the group consisting of $Ch_2Cl_2$, $CHCl_3$, EtO/Ac, ether, acetone, MeOH, EtOH and $CH_3CN$.

4. A process as claim 1 wherein the solvents used for hot extraction are removed at a temperature in the range of 35–40° C.

5. A process as claim 1 wherein the process is carried out in a period of up to 24 hours.

* * * * *